(12) United States Patent
Suyama

(10) Patent No.: US 11,134,829 B2
(45) Date of Patent: Oct. 5, 2021

(54) IMAGE PICKUP APPARATUS, ENDOSCOPE, AND METHOD FOR MANUFACTURING IMAGE PICKUP APPARATUS

(71) Applicant: OLYMPUS CORPORATION, Tokyo (JP)

(72) Inventor: Takuro Suyama, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 445 days.

(21) Appl. No.: 16/118,865

(22) Filed: Aug. 31, 2018

(65) Prior Publication Data

US 2018/0368661 A1 Dec. 27, 2018

Related U.S. Application Data

(63) Continuation of application No. PCT/JP2016/058144, filed on Mar. 15, 2016.

(51) Int. Cl.
*A61B 1/00* (2006.01)
*A61B 1/04* (2006.01)
(Continued)

(52) U.S. Cl.
CPC .............. *A61B 1/0011* (2013.01); *A61B 1/04* (2013.01); *A61B 1/051* (2013.01);
(Continued)

(58) Field of Classification Search
CPC ..... H01L 2224/50; H01L 24/50; H01L 24/86; H01L 23/49822; H01L 31/0224; A61B 1/0011; A61B 1/051; H05K 1/0271
See application file for complete search history.

(56) References Cited

U.S. PATENT DOCUMENTS 10,334,143 B2 * 6/2019 Nakayama .............. H01L 24/50
2011/0199473 A1 * 8/2011 Kojima .................... A61B 1/05
348/76

(Continued)

FOREIGN PATENT DOCUMENTS

EP 2905954 A1 8/2015
EP 2923635 A1 9/2015
(Continued)

OTHER PUBLICATIONS

International Search Report dated May 31, 2016 issued in PCT/JP2016/058144.

*Primary Examiner* — Alexandra L Newton
*Assistant Examiner* — Jae Woo
(74) *Attorney, Agent, or Firm* — Scully, Scott, Murphy & Presser, P.C.

(57) ABSTRACT

An image pickup apparatus includes an image pickup device including a wiring connecting a first electrode on a light receiving surface and a second electrode on a rear surface, a first wiring board including a distal end surface, from which a flying lead protrudes, arranged to oppose the rear surface of the image pickup device, a second wiring board including a second main surface to which an upper surface of the first wiring board is made to adhere and including a distal end surface arranged to oppose the rear surface, in which the flying lead is bent and bonded to the second electrode, and a sealing member sealing a bonding section between the second electrode and the flying lead and an adhesion member that makes the distal end surface of the second wiring board and the rear surface adhere to each other are composed of integral curable resin.

6 Claims, 5 Drawing Sheets

(51) Int. Cl.
*A61B 1/05* (2006.01)
*H01L 23/498* (2006.01)
*H01L 23/00* (2006.01)
*H01L 27/146* (2006.01)

(52) U.S. Cl.
CPC .... *H01L 23/4985* (2013.01); *H01L 23/49822* (2013.01); *H01L 23/49838* (2013.01); *H01L 24/50* (2013.01); *H01L 24/86* (2013.01); *H01L 24/92* (2013.01); *H01L 27/14683* (2013.01); *H01L 2224/50* (2013.01); *H01L 2224/86947* (2013.01); *H01L 2224/92175* (2013.01)

(56) References Cited

U.S. PATENT DOCUMENTS

| | | | | |
|---|---|---|---|---|
| 2013/0214375 A1* | 8/2013 | Dai | ............... | H01L 27/14618 257/459 |
| 2015/0014805 A1* | 1/2015 | Yamada | ............ | H01L 27/14625 257/443 |
| 2015/0207965 A1* | 7/2015 | Fujimori | ............... | A61B 1/051 348/65 |
| 2015/0305606 A1* | 10/2015 | Kaneko | ............... | A61B 1/051 348/76 |
| 2016/0037029 A1* | 2/2016 | Igarashi | ............... | H05K 1/185 348/65 |
| 2016/0054559 A1* | 2/2016 | Igarashi | ............... | H04N 5/2253 348/68 |

FOREIGN PATENT DOCUMENTS

| | | |
|---|---|---|
| EP | 2987448 A1 | 2/2016 |
| JP | 2011-249870 A | 12/2011 |
| JP | 2013-098182 A | 5/2013 |
| JP | 2013-219468 A | 10/2013 |
| JP | 2014-075764 A | 4/2014 |
| JP | 2014-210041 A | 11/2014 |
| JP | 2015-008901 A | 1/2015 |
| JP | 5750642 B1 | 7/2015 |
| WO | WO 2013/150813 A1 | 10/2013 |
| WO | WO 2014/054419 A1 | 4/2014 |
| WO | WO 2014/171482 A1 | 10/2014 |
| WO | WO 2014/208206 A1 | 12/2014 |
| WO | WO 2015/050044 A1 | 4/2015 |

* cited by examiner

IMAGE PICKUP APPARATUS, ENDOSCOPE, AND METHOD FOR MANUFACTURING IMAGE PICKUP APPARATUS

CROSS REFERENCE TO RELATED APPLICATION

This application is a continuation application of PCT/JP2016/058144 filed on Mar. 15, 2016, the entire contents of which are incorporated herein by this reference.

BACKGROUND OF INVENTION

1. Field of the Invention

The present invention relates to an image pickup apparatus including an image pickup device, a first wiring board including a flying lead bonded to an electrode on a rear surface of the image pickup device, and a second wiring board including a second main surface made to adhere to the first wiring board and a distal end surface made to adhere to the image pickup device, an endoscope including the image pickup apparatus in a distal end rigid portion, and a method for manufacturing the image pickup apparatus.

2. Description of the Related Art

An image pickup apparatus placed in a distal end rigid portion of an endoscope has been strongly desired to be miniaturized to achieve minimal invasiveness.

Japanese Patent Application Laid-Open Publication No. 2015-8901 discloses an image pickup unit in which a bonding section between an electrode on a light receiving surface of an image pickup device and an inner lead (flying lead) of a first substrate has been sealed with sealing resin while a distal end surface of a second substrate to which the first substrate has been made to adhere and a rear surface of the image pickup device have been made to adhere to and fixed to each other with an adhesive. The first substrate is a flexible wiring board, and the second substrate is a non-flexible wiring board thicker than the first substrate.

Japanese Patent Application Laid-Open Publication No. 2014-75764 discloses an image pickup apparatus manufactured using a wafer level chip size package (W-CSP) technique. In a method for manufacturing a W-CSP type image pickup apparatus, a plurality of light receiving sections and a plurality of external electrodes respectively electrically connected to the light receiving sections are first formed on a light receiving surface of a semiconductor wafer. A glass wafer is made to adhere to the light receiving surface of the semiconductor wafer, to produce a bonded wafer. A wiring which reaches, from the light receiving surface of the bonded wafer, an opposing rear surface is formed and the external electrodes on the light receiving surface and an electrode on the rear surface are electrically connected to each other. The bonded wafer is cut, to produce a plurality of image pickup devices. An electrode on a wiring board is bonded to electrodes on rear surfaces of the image pickup devices.

The above-described image pickup apparatus is inserted into a frame with the wiring board only bonded to the image pickup devices, and the frame is then filled with sealing resin.

SUMMARY OF THE INVENTION

An image pickup apparatus according to an aspect of the present invention includes an image pickup device including a light receiving surface and a rear surface opposing the light receiving surface and including a wiring that connects a first electrode on the light receiving surface and a second electrode on the rear surface, a flexible member including an upper surface, a lower surface opposing the upper surface, and an end surface perpendicular to the upper surface, the end surface from which a flying lead protrudes being arranged to oppose the rear surface of the image pickup device, and a non-flexible member including a first main surface, a second main surface opposing the first main surface, and a distal end surface perpendicular to the first main surface, the upper surface of the flexible member being made to adhere to the second main surface, and the distal end surface being arranged to oppose the rear surface of the image pickup device, in which the flying lead is bent, and a distal end portion of the flying lead is bonded to the second electrode in the image pickup device, a bonding section between the second electrode in the image pickup device and the distal end portion of the flying lead is sealed with a sealing member, the distal end surface of the non-flexible member is made to adhere to the rear surface of the image pickup device with an adhesion member interposed between the surfaces, and the sealing member and the adhesion member are composed of integral curable resin.

An endoscope according to another aspect includes in a distal end rigid portion an image pickup apparatus including an image pickup device including a light receiving surface and a rear surface opposing the light receiving surface and including a wiring that connects a first electrode on the light receiving surface and a second electrode on the rear surface, a flexible member including an upper surface, a lower surface opposing the upper surface, and an end surface perpendicular to the upper surface, the end surface from which a flying lead protrudes being arranged to oppose the rear surface of the image pickup device, and a non-flexible member including a first main surface, a second main surface opposing the first main surface, and a distal end surface perpendicular to the first main surface, the upper surface of the flexible member being made to adhere to the second main surface, and the distal end surface being arranged to oppose the rear surface of the image pickup device, in which the flying lead is bent, and a distal end portion of the flying lead is bonded to the second electrode in the image pickup device, a bonding section between the second electrode in the image pickup device and the distal end portion of the flying lead is sealed with a sealing member, the distal end surface of the non-flexible member is made to adhere to the rear surface of the image pickup device with an adhesion member interposed between the surfaces, and the sealing member and the adhesion member are composed of integral curable resin.

A method for manufacturing an image pickup apparatus according to still another aspect including an image pickup device including a light receiving surface and a rear surface opposing the light receiving surface and including a wiring that connects a first electrode on the light receiving surface and a second electrode on the rear surface, a flexible member including an end surface from which a flying lead protrudes, and a non-flexible member to which the flexible member is made to adhere, the method including the steps of bonding the second electrode in the image pickup device and a distal end portion of the flying lead to each other, making the flexible member adhere to the non-flexible member while bending the flying lead, and subjecting to curing treatment integral curable resin composing a sealing member that seals a bonding section between the second electrode and the

DETAILED DESCRIPTION OF THE PREFERRED EMBODIMENT(S)

First Embodiment

Figure 1:
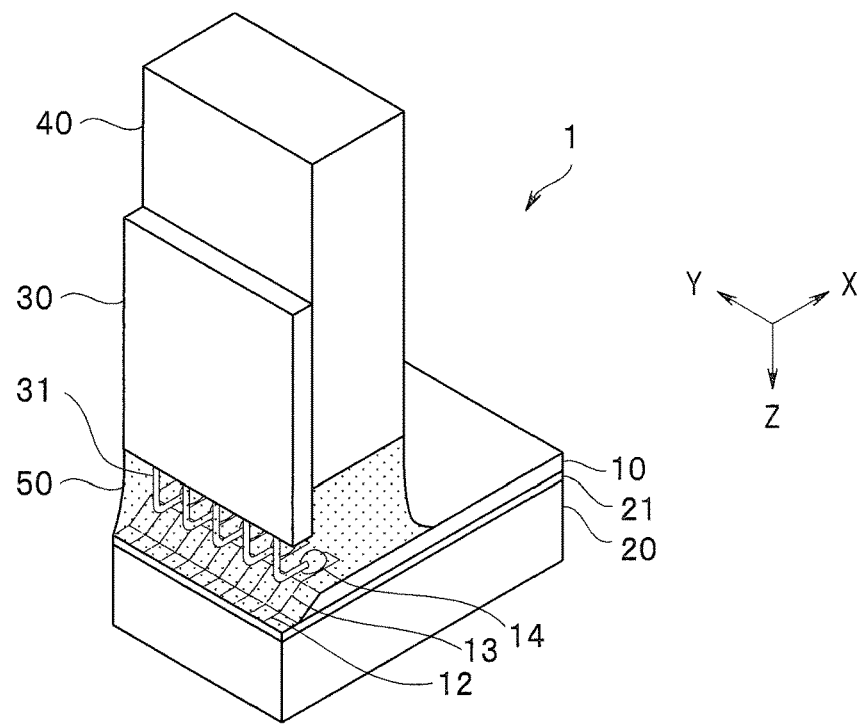
FIG. 1 is a perspective view of an image pickup apparatus according to a first embodiment.

An image pickup apparatus 1 according to a first embodiment of the present invention will be described below with reference to the drawings. Note that the drawings are schematic, and a relationship between a thickness and a width of each of members, a proportion of the thickness of each of the members, the number of electrodes, an arrangement pitch of the electrodes, and the like differ from the respective actual ones. Portions which differ in dimensional relationship and proportion among the drawings are respectively included in the drawings. Further, illustration of some of components, e.g., a silicon oxide layer on a surface of an image pickup device is omitted.

Figure 2:
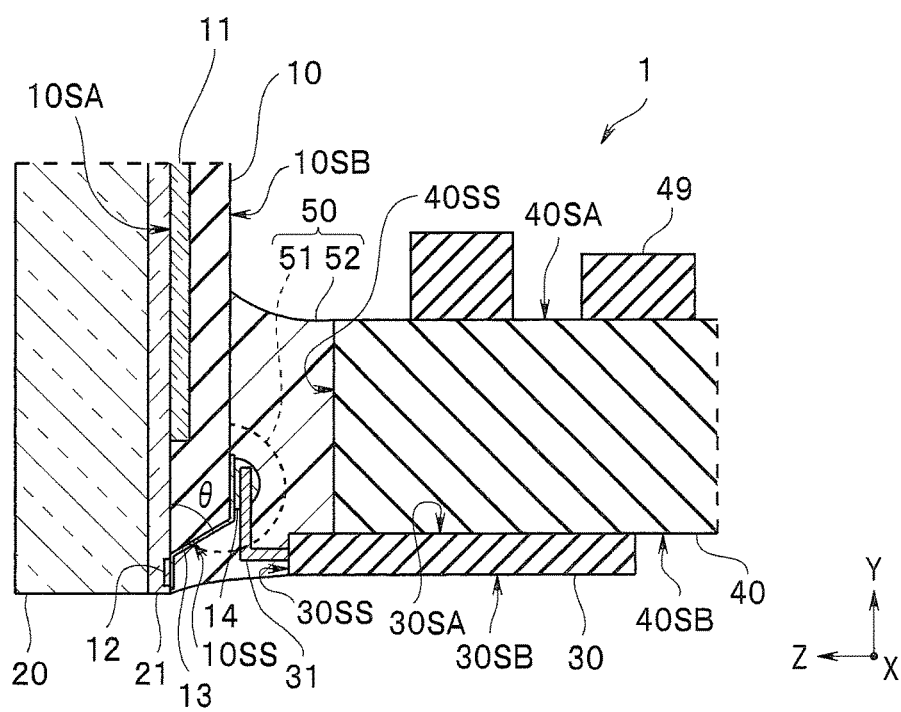
FIG. 2 is a cross-sectional view along a line II-II illustrated in FIG. 1 of the image pickup apparatus according to the first embodiment.

As illustrated in FIGS. 1 and 2, the image pickup apparatus 1 includes an image pickup device 10, a cover glass 20, a first wiring board 30, a second wiring board 40, and curable resin 50. A signal cable (not illustrated) is bonded to the second wiring board 40.

The image pickup device 10 composed of silicon includes a light receiving surface 10SA on which a light receiving section 11 is formed, a rear surface 10SB opposing the light receiving surface 10SA, and an inclined surface 10SS inclined with respect to the light receiving surface 10SA by an acute angle θ. First electrodes 12 electrically connected to the light receiving section 11 are lined up on the light receiving surface 10SA.

The first electrode 12 is covered with the cover glass 20 with an adhesion layer 21 interposed between the first electrode 12 and the cover glass 20. However, the first electrode 12 includes a rear surface exposed to the rear surface 10SB side, and is connected to a second electrode 14 on the rear surface 10SB via a wiring 13.

The first wiring board 30 as a flexible member includes an upper surface 30SA, a lower surface 30SB opposing the upper surface 30SA, and a distal end surface 30SS perpendicular to the upper surface 30SA. A plurality of flying leads 31 protrude from the distal end surface 30SS.

The second wiring board 40 as a non-flexible member includes a first main surface 40SA, a second main surface 40SB opposing the first main surface 40SA, and a distal end surface 40SS perpendicular to the first main surface 40SA. The upper surface 30SA of the first wiring board 30 is made to adhere to the second main surface 40SB of the second wiring board 40.

The distal end surface 40SS of the second wiring board 40 is made to adhere to the rear surface 10SB of the image pickup device 10 with an adhesion member 52 composed of curable resin interposed between the surfaces. That is, the distal end surface 30SS of the first wiring board 30 and the distal end surface 40SS of the second wiring board 40 are arranged parallel to the rear surface 10SB of the image pickup device 10.

Accordingly, the first wiring board 30 and the second wiring board 40 are entirely arranged within an area inside the image pickup device 10, i.e., within a projection plane of the image pickup device 10 when viewed in a planar view in a thickness direction (Z direction) of the image pickup device 10. Further, a not illustrated signal cable does not protrude more outward than an external form of the image pickup device 10. Accordingly, the image pickup apparatus 1 has a small diameter.

Note that if the first wiring board 30 and the second wiring board 40 are entirely arranged within the projection plane of the image pickup device 10, the distal end surface 30SS of the first wiring board 30 and the distal end surface 40SS of the second wiring board 40 are not parallel to the rear surface 10SB of the image pickup device 10 but may be inclined. That is, the distal end surface 30SS of the first wiring board 30 and the distal end surface 40SS of the second wiring board 40 may be arranged to oppose the rear surface 10SB of the image pickup device 10.

Each of the flying leads 31 in the first wiring board 30 is bent at a substantially right angle, and a distal end portion of the flying lead 31 is bonded to the second electrode 14 in the image pickup device 10. A bonding section between the second electrode 14 in the image pickup device 10 and the distal end portion of the flying lead 31 is sealed with a sealing member 51 composed of curable resin.

In the image pickup apparatus 1, the sealing member 51 and the adhesion member 52 are composed of integral curable resin 50. That is, adhesion and fixing of the second wiring board 40 to the image pickup device 10 and sealing of the bonding section between the second electrode 14 and the flying lead 31 are simultaneously performed, as described below. In other words, the sealing member 51 and the adhesion member 52 are simultaneously subjected to curing treatment.

The image pickup apparatus 1 is easily manufactured because the sealing member 51 and the adhesion member 52 are composed of the integral curable resin 50. Further, the image pickup apparatus 1 may not be damaged even if stress is applied to the image pickup apparatus 1 because a sealing section is mechanically reinforced by the sealing member 51, and is high in reliability.

Note that it cannot be definitely specified in terms of a structure or a characteristic that the sealing member 51 and the adhesion member 52 have been simultaneously subjected to curing treatment. Further, it is also impossible from a current analysis technique to specify that the sealing member 51 and the adhesion member 52 have been simultaneously subjected to curing treatment by analyzing the structure based on a measurement.

Method for Manufacturing Image Pickup Apparatus

Figure 3:
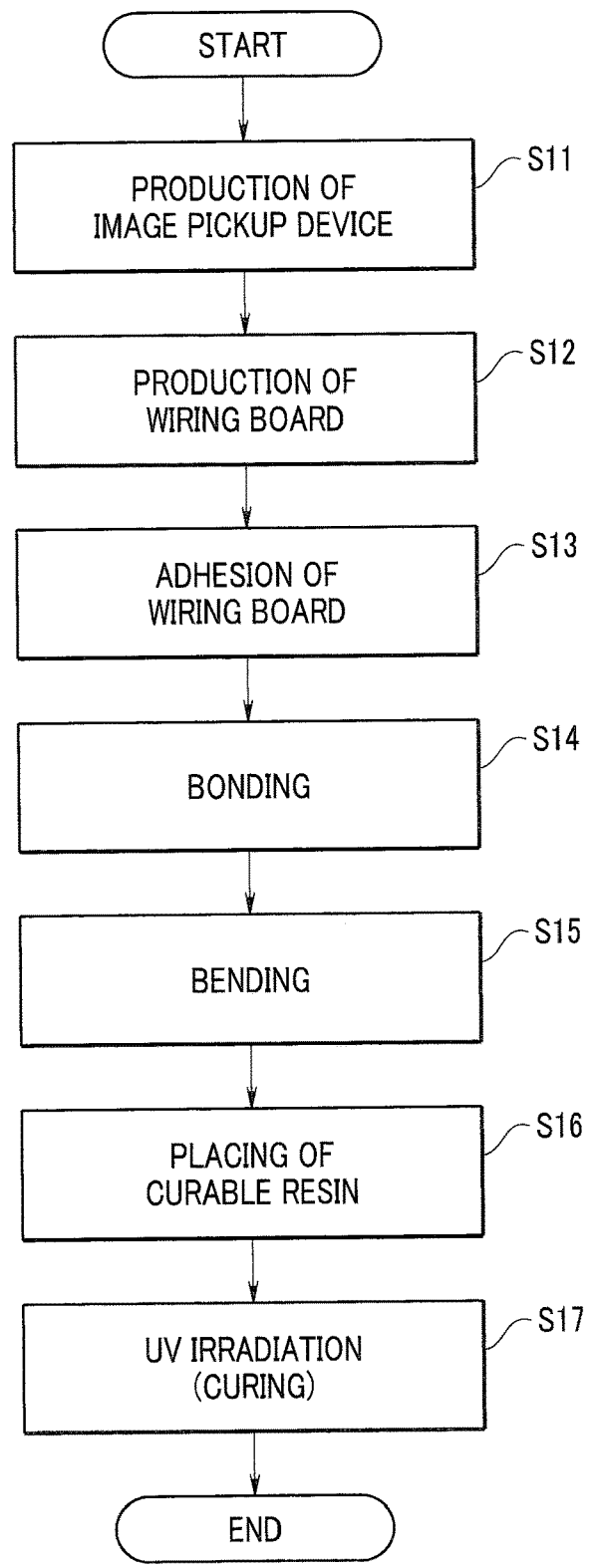
FIG. 3 is a flowchart for describing a method for manufacturing the image pickup apparatus according to the first embodiment.

A method for manufacturing the image pickup apparatus 1 will be described along a flowchart of FIG. 3.

<Step S11>Production of Image Pickup Device

As the image pickup device 10, many image pickup devices are manufactured through a wafer process using a semiconductor manufacturing technique. A plurality of light receiving sections 11 each composed of a CMOS (complementary metal oxide semiconductor) image sensor, a CCD (charge coupled device), or the like are formed on a silicon wafer. A plurality of first electrodes 12, which feed electrical signals to the light receiving sections 11 and transmit image pickup signals from the light receiving sections 11, are respectively placed around the light receiving sections 11.

A glass wafer is made to adhere to a light receiving surface of the silicon wafer with an adhesive composed of transparent ultraviolet curable resin, to produce a bonded wafer. Note that a microlens array may be placed on the light receiving section 11, to make the periphery of the light receiving section 11 adhere to the microlens array with an adhesive having a light shielding property.

A through trench including an inclined surface 10SS as a wall surface is formed such that a rear surface of the first electrode 12 is exposed to a rear surface side of the bonded wafer. Anisotropic etching can be preferably used to faun the through trench including the inclined surface 10SS. Although anisotropic etching is desirably a wet etching method using a tetramethylammonium hydroxide (TMAH) solution, a potassium hydroxide (KOH) solution, or the like, a dry etching method such as reactive ion etching (RIE) or chemical dry etching (CDE) can also be used.

If a silicon substrate including a (100) surface as a light receiving surface 10SA is used as the image pickup device 10, for example, anisotropic etching in which an etching speed of a (111) surface is lower than an etching speed of the (100) surface is performed. Accordingly, the wall surface of the through trench becomes the (111) surface, and becomes the inclined surface 10SS with an acute angle $\theta$ of 54.74° to the (100) surface as the light receiving surface 10SA.

Then, a wiring 13 is placed from the rear surface of the first electrode 12 exposed to a rear surface 10SB to the rear surface 10SB. A second electrode 14 is placed in the wiring 13 to the rear surface 10SB. The second electrode 14 is, for example, a solder bump or a gold bump formed using a frame plating method or a paste printing method.

Note that the first electrode 12 and the second electrode 14 may be connected to each other via not the wiring 13 but a through wiring.

The bonded wafer is cut to produce a W-CSP type image pickup device 10 in which the light receiving surface 10SA is covered with a cover glass 20 and the second electrode 14 is placed on the rear surface 10SB.

<Step S12>Production of Wiring Board

A first wiring board 30 is a flexible wiring board including a plurality of wirings using polyimide, for example, as an insulating layer. In the first wiring board 30, a flying lead 31 protrudes from a distal end surface 30SS. That is, the first wiring board 30 is bonded to the image pickup device 10 using a TAB (tape automated bonding) technique.

The flying lead 31 is a rod-shaped metal conductor formed by selectively detaching an insulating layer or the like around the wirings in the wiring board 30, although also referred to as an inner lead in a lead frame. The wiring board 30 may be a two-sided wiring board or a multilayer wiring board.

On the other hand, a second wiring board 40 is a non-flexible rigid wiring board. That is, the second wiring board 40 has a large thickness (Y-axis dimension) of 300 µm, for example, and an area of a distal end surface 40SS of the second wiring board 40 is large. An electronic component 49 such as a chip capacitor is mounted on a first main surface 40SA of the second wiring board 40. Note that the second wiring board 40 may be a component-incorporating wiring board.

<Step S13>Adhesion of Wiring Board

An upper surface 30SA of the first wiring board 30 and a second main surface 40SB of the second wiring board 40 are made to adhere to each other. Simultaneously with the adhesion, an electrode on the upper surface of the first wiring board 30 and an electrode on the second main surface of the second wiring board 40 are bonded to each other, and are electrically connected to each other.

<Step S14>Bonding of Flying Lead

Figure 4B:
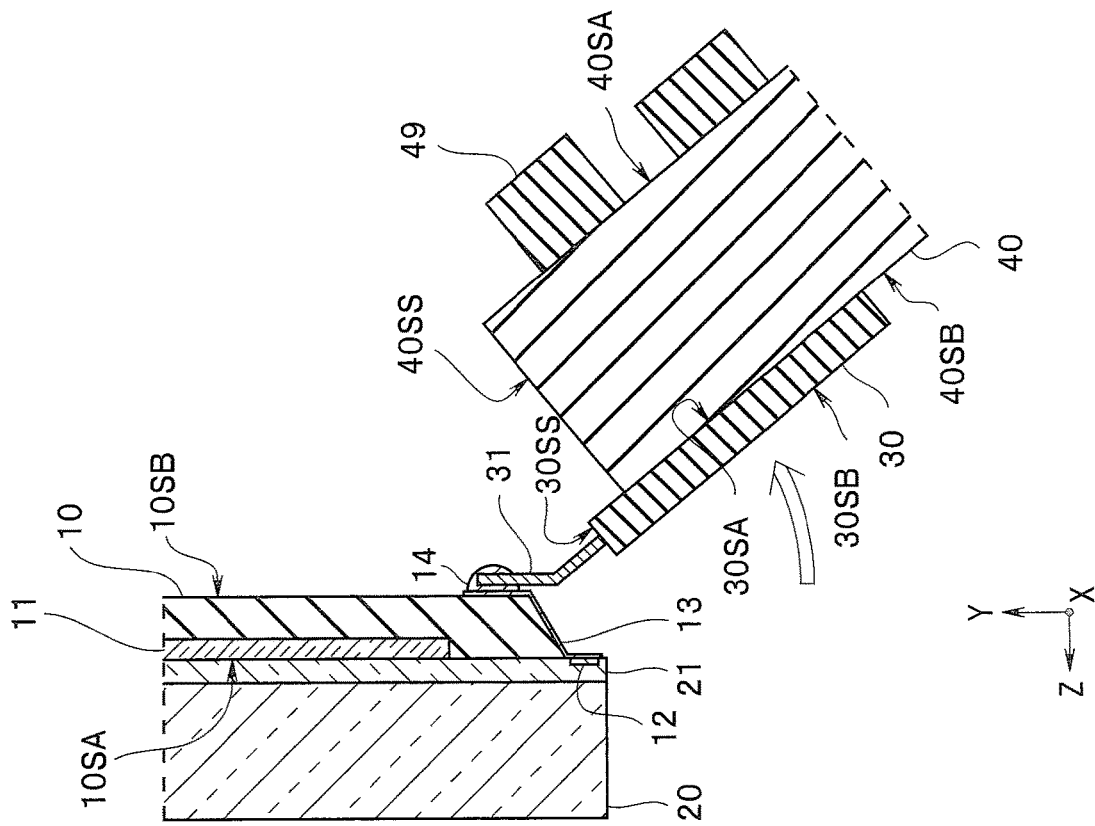
FIG. 4B is a cross-sectional view for describing the method for manufacturing the image pickup apparatus according to the first embodiment.
Figure 4A:
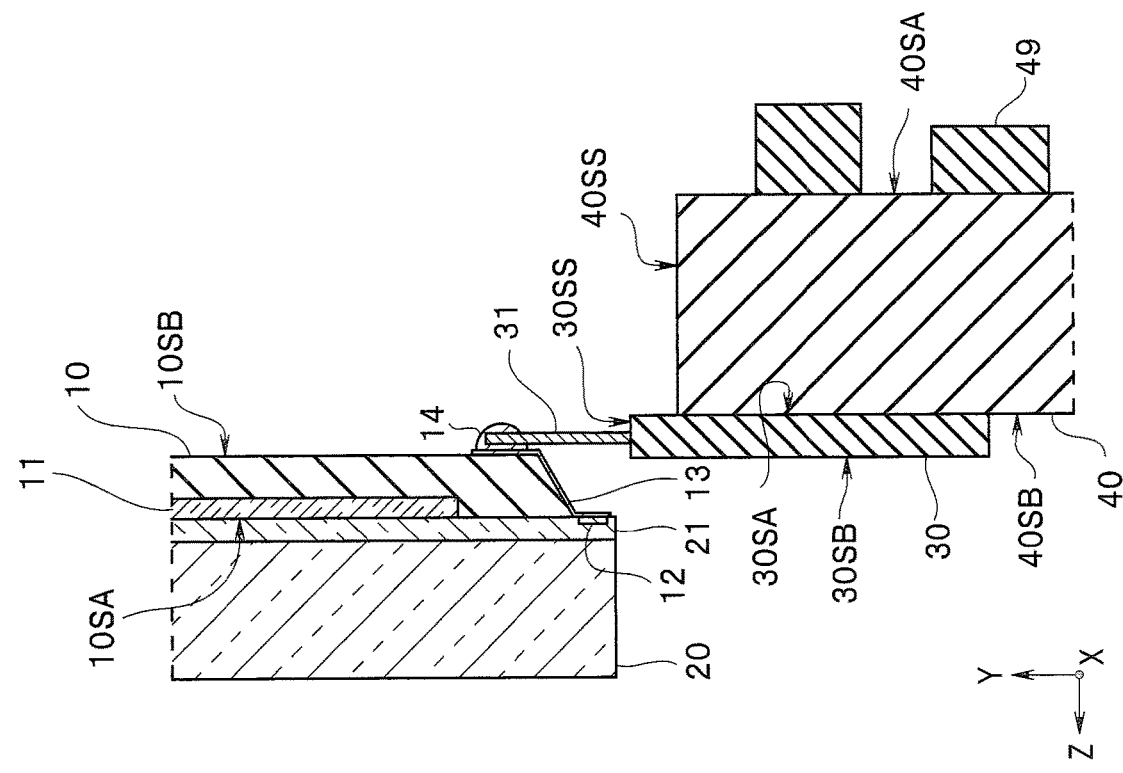
FIG. 4A is a cross-sectional view for describing the method for manufacturing the image pickup apparatus according to the first embodiment.

As illustrated in FIG. 4A, the flying lead 31 in the first wiring board 30 and the second electrode 14 on the rear surface 10SB of the image pickup device 10 are bonded to each other.

The bonding is solder bonding or ultrasonic bonding.

<Step S15>Bending of Flying Lead

As illustrated in FIG. 4B, the flying lead 31 is bent such that a distal end surface 40SS of the second wiring board 40 is parallel to the rear surface 10SB of the image pickup device 10.

<Step S16>Placing of Curable Resin

Figure 5:
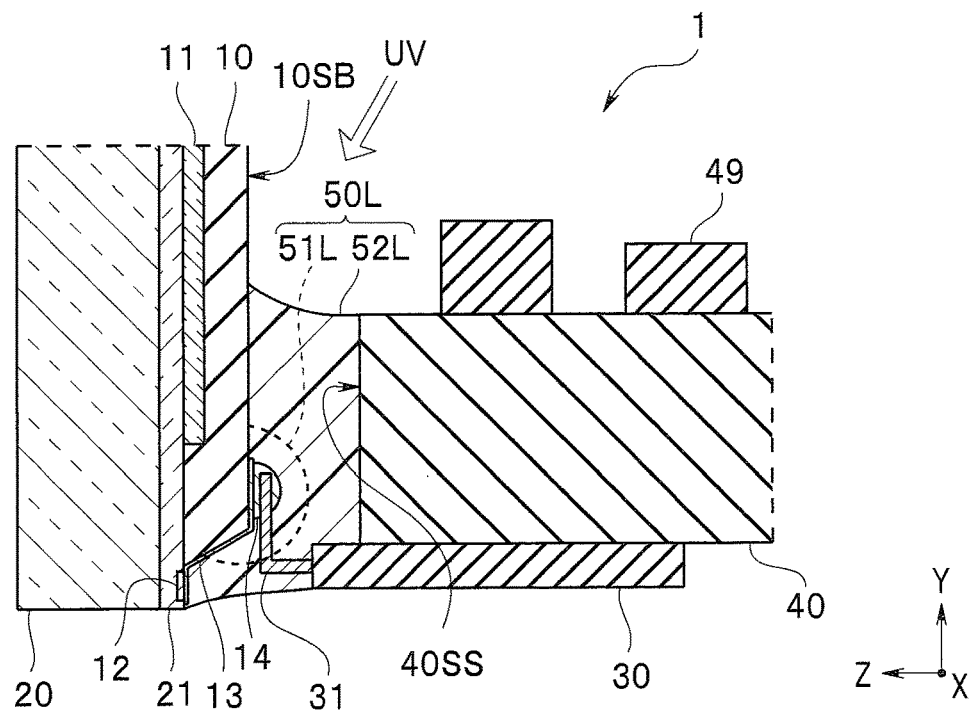
FIG. 5 is a cross-sectional view for describing the method for manufacturing the image pickup apparatus according to the first embodiment.
Figure 6:
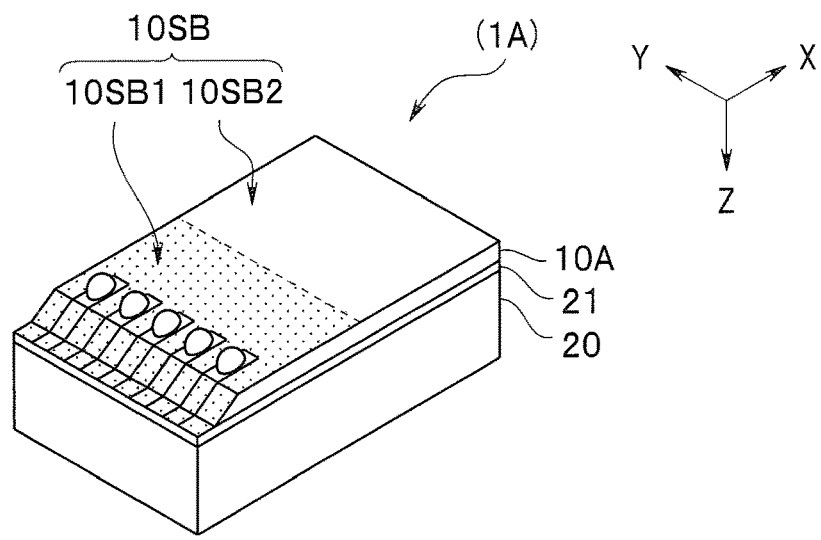
FIG. 6 is a perspective view of an image pickup device for describing a method for manufacturing an image pickup apparatus according to a second embodiment.

As illustrated in FIG. 5, uncured and liquid curable resin 50L is injected between the rear surface 10SB of the image pickup device 10 and the distal end surface 40SS of the second wiring board 40. At this time, not only an adhesion section between the rear surface 10SB and the distal end surface 40SS but also a bonding section between the flying lead 31 and the second electrode 14 is covered with the curable resin 50L. The sealing member 51L and the adhesion member 52L are composed of integral curable resin 50L.

Although thermosetting resin or ultraviolet curable resin can be used as the curable resin, the ultraviolet curable resin is preferably used from the viewpoint of workability. Silicone-based resin, epoxy-based resin, or acrylic-based resin, for example, is used as the ultraviolet curable resin.

Note that uncured curable resin may be injected into a predetermined portion before a flying lead bending process.

<Step S17>Curing Treatment

As illustrated in FIG. 5, curing treatment of irradiating the uncured and liquid curable resin 50L with ultraviolet rays (UV) is performed. By the curing treatment, the curable resin 50L is solidified so that a bonding section is sealed and an adhesion section is fixed.

According to the method for manufacturing the image pickup apparatus 1, the curing treatment for sealing the bonding section and the curing treatment for fixing the adhesion section are simultaneously performed. Accordingly, the image pickup apparatus 1 is easily manufactured.

Note that the image pickup apparatus 1 is inserted into a frame of an insertion distal end portion of an endoscope, for example, as described below. In the image pickup apparatus 1 manufactured using the image pickup apparatus manufacturing method according to the embodiment may not be damaged even if stress is applied to the image pickup apparatus when inserted into the frame, for example, because the bonding section is sealed with curable resin and fixed, and is high in reliability.

Second Embodiment

An image pickup apparatus 1A according to a modification as a second embodiment will be described below. Since the image pickup apparatus 1A is similar to and identical in effect to the image pickup apparatus 1, components having the same functions are respectively assigned the same reference numerals, and hence description of the components is not repeated.

The image pickup apparatus 1A is the same in appearance as and is not easily distinguished from the image pickup apparatus 1. However, in the image pickup apparatus 1A, an area where curable resin 50 is placed on a rear surface 10SB of an image pickup device 10A is an area in a previously set range, e.g., up to 250 μm that is half a dimension in a length direction (X direction).

Uncured and liquid curable resin 50L differs in wettability depending on a state of a surface on which the curable resin has been placed. The "wettability" is an affinity of a liquid for a solid surface, and is represented as a hydrophilic property or a hydrophobic property when the liquid is water. The "wettability" can be quantified by a contact angle $\phi$ when the liquid is dropped on the surface. The smaller the contact angle $\phi$ is, the more greatly the liquid placed on the surface spreads. On the other hand, the larger the contact angle $\phi$ is, the less easily the liquid placed on the surface spreads.

In the image pickup device 10A, the uncured and liquid curable resin 50L exhibits a similar property to a property of water. That is, the curable resin 50L easily spreads on a hydrophilic surface, and does not easily spread on a hydrophobic surface.

In the image pickup apparatus 1A, a sealing section and an adhesion section are simultaneously subjected to curing treatment. Accordingly, a relatively large amount of curable resin 50L needs to be injected. However, the curable resin 50L may not only insufficiently seal the sealing section because an amount of resin remaining in the sealing section decreases but also adversely affect bonding of a signal cable when the curable resin 50L greatly spreads on the rear surface 10SB. The curable resin 50L excessively injected prevents the image pickup apparatus 1 from decreasing in diameter when the curable resin 50L spreads on a side surface of the image pickup device 10A. The curable resin 50L also adversely affects a picked-up image when the curable resin 50L spreads to a light receiving surface 10SA.

Accordingly, a method for manufacturing the image pickup apparatus 1A includes a step of subjecting to hydrophilic treatment a surface of an area, where the curable resin 50 is placed, of the image pickup device 10A. Accordingly, a contact angle $\phi 1$ of an area 10SB1 where the curable resin 50 is placed with the uncured and liquid curable resin 50L is smaller than a contact angle $\phi 2$ of an area 10SB2 where the curable resin 50 is not placed with the cured and liquid curable resin 50L.

Although the contact angle $\phi 2$ of the area 10SB2 where the curable resin 50 is not placed is 20° to 30°, for example, the contact angle $\phi 1$ of the area 10SB1 where the curable resin 50 is placed is preferably 10° or less.

The hydrophilic treatment is performed by ultraviolet irradiation, oxygen plasma irradiation, hydrophilic polymer coating, or blast treatment, for example. Although the rear surface 10SB is covered with a silicon oxide film, for example, a hydroxyl group (—OH) is formed on the surface when an Si bond is ring-opened by ultraviolet treatment and is combined with water in the air. To give stronger hydrophilicity, a hydrophilic functional group such as a carboxyl group may be introduced into the surface by CVD, for example.

An area where the curable resin 50 is not desired to be placed, in other words, an area where it is not desirable for the curable resin 50 to spread, is covered with a resist mask or the like not to be irradiated with ultraviolet rays before the hydrophilic treatment. Note that the hydrophilic treatment may be performed in a wafer process when an image pickup device is produced or may be performed after the image pickup device is divided into individual pieces if the uncured curable resin 50L has not been placed.

In the image pickup apparatus 1A, even if the curable resin 50L is excessively injected into the image pickup apparatus 1A, the curable resin 50L may be prevented from greatly spreading on the rear surface 10SB to insufficiently seal the sealing section or prevented from spreading to the side surface or the light receiving surface of the image pickup device 10A.

Third Embodiment

An endoscope 9 according to a third embodiment will be described below. Image pickup apparatuses 1 and 1A in the endoscope 9 are respectively the same as the image pickup apparatuses 1 and the like according to the above-described embodiments, and hence description of the image pickup apparatuses is not repeated. The endoscope 9 including the image pickup apparatus 1 will be described as an example below.

Figure 7:
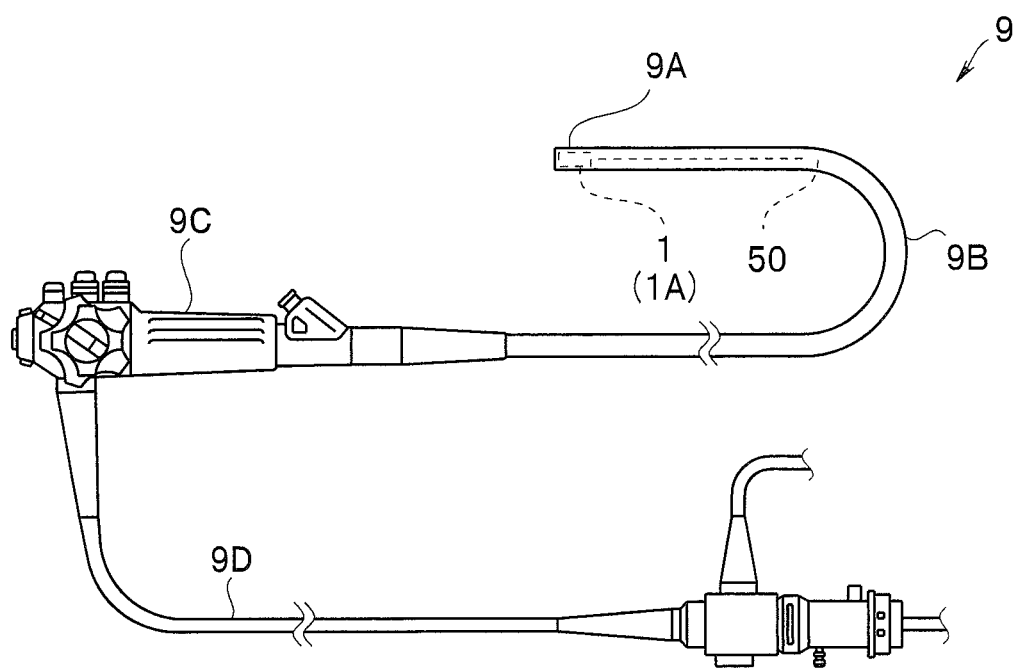
FIG. 7 is a perspective view of an endoscope according to a third embodiment.

As illustrated in FIG. 7, the endoscope 9 includes an insertion section 9B including a distal end rigid portion 9A in which the image pickup apparatus 1 including an image pickup device composed of a large number of pixels is placed, an operation section 9C placed on the side of a proximal end of the insertion section 9B, and a universal code 9D extending from the operation section 9C.

The endoscope 9 is minimally invasive because the image pickup apparatus 1 having a small diameter is placed in the distal end rigid portion of the insertion section. Further, the image pickup apparatus 1 may not be damaged even if stress is applied to the image pickup apparatus 1 when inserted into the distal end rigid portion or when used because a bonding section is sealed with curable resin and fixed, and is high in reliability.

The present invention is not limited to the above-described embodiments or modification, for example, but various changes, alterations, combinations, and the like can be made without departing from the scope and spirit of the present invention.

What is claimed is:

1. An image pickup apparatus comprising:
an image pickup device including an image sensor disposed on a distal surface and a proximal surface opposing the distal surface, the image pickup device including a wiring that electrically connects a first electrode on the distal surface to a second electrode on the proximal surface;
a flexible member including an upper surface, a lower surface opposing the upper surface, and a first distal end surface disposed between and adjacent to the upper surface and the lower surface, the first distal end surface being arranged to oppose the proximal surface of the image pickup device;
a non-flexible member including a first main surface, a second main surface opposing the first main surface, and a second distal end surface disposed between and adjacent to the first main surface and the second main surface, the upper surface of the flexible member being adhered to the second main surface of the non-flexible member, and the second distal end surface being arranged to oppose the proximal surface of the image pickup device,
a flying lead protruding from the first distal end surface of the flexible member, the flying lead being bent such that a distal end portion of the flying lead is bonded to the second electrode on the proximal surface of the image pickup device, and
an integral curable resin disposed:
between the second electrode on the proximal surface of the image pickup device and the distal end portion of the flying lead to seal a connection between the second electrode and the distal end portion, and
between the second distal end surface of the non-flexible member and the proximal surface of the image pickup device to adhere the second distal end surface to the proximal surface.

2. The image pickup apparatus according to claim 1, wherein a contact angle of an area of the image pickup device where the curable resin is placed with the curable resin in an uncured liquid state is smaller than a contact angle of an area of the image pickup device where the curable resin is not placed with the curable resin in an uncured liquid state.

3. The image pickup apparatus according to claim 1, wherein the curable resin disposed between the second electrode and the distal end portion and the curable resin disposed between the second distal end surface of the non-flexible member and the proximal surface of the image pickup device are simultaneously subjected to curing treatment.

4. An endoscope comprising:
an insertion section having a distal end rigid portion; and
the image pickup apparatus according to claim 1 disposed in the distal end rigid portion of the insertion section.

5. The image pickup apparatus according to claim 1, wherein the integral curable resin is further disposed between the second electrode on the image pickup device and the first distal end surface of the flexible member.

6. The image pickup apparatus according to claim 5, wherein the integral curable resin disposed between the second electrode and the distal end portion, the integral curable resin disposed between the second distal end surface and the proximal surface and the integral curable resin disposed between the second electrode and the first distal end surface are simultaneously subjected to curing treatment.

* * * * *